United States Patent [19]

Pappas et al.

[11] Patent Number: 5,159,115

[45] Date of Patent: Oct. 27, 1992

[54] CATALYZED GAS-PHASE MONO N-ALKYLATION OF AROMATIC PRIMARY AMINES

[75] Inventors: Peter G. Pappas; Judith B. Melville, both of Downers Grove, Ill.

[73] Assignee: Amoco Corporation, Chicago, Ill.

[21] Appl. No.: 397,379

[22] Filed: Aug. 18, 1989

[51] Int. Cl.$^5$ ............................................. C07C 209/18
[52] U.S. Cl. .................................... 564/401; 564/399; 564/402
[58] Field of Search ......................... 564/399, 401, 402

[56] References Cited

U.S. PATENT DOCUMENTS

| | | | |
|---|---|---|---|
| 3,384,667 | 5/1968 | Hamilton | 260/585 |
| 4,183,868 | 1/1980 | Radimerski et al. | 260/573 |
| 4,268,420 | 5/1981 | Klotz | 252/432 |
| 4,585,641 | 4/1986 | Barri et al. | 423/331 |
| 4,670,617 | 6/1987 | De Simone et al. | 585/467 |

FOREIGN PATENT DOCUMENTS

| | | |
|---|---|---|
| 53-90227 | 8/1978 | Japan . |
| 1291548 | 12/1986 | Japan . |
| 0673433 | 4/1950 | United Kingdom . |
| 2024790 | 1/1980 | United Kingdom . |

OTHER PUBLICATIONS

Onaka et al. *Chem. Abst.*

*Primary Examiner*—Richard L. Raymond
*Assistant Examiner*—Peter G. O'Sullivan
*Attorney, Agent, or Firm*—William H. Magidson; Robert J. Wagner

[57] ABSTRACT

Described are processes for the gas-phase mono N-alkylation of an aniline or an aminonaphthalene using a $C_1$ to $C_5$ aliphatic alcohol or ether over certain catalyst compositions based upon crystalline molecular sieves or amorphous silica-aluminas.

5 Claims, No Drawings

CATALYZED GAS-PHASE MONO N-ALKYLATION OF AROMATIC PRIMARY AMINES

This is a continuation of application Ser. No. 068,890, filed Jun. 30, 1987, now abandoned.

Background of the Invention

This invention relates to catalyst compositions comprising crystalline molecular sieves and amorphous silica-alumina compositions and to gas-phase processes for selectively mono N-alkylating aromatic primary amines by contacting such an aromatic primary amine and an alkylating agent under N-alkylation conditions with said compositions. More particularly, the invention relates to catalyst compositions comprising high-surface-area, crystalline molecular sieves and amorphous silica-aluminas alone or, in the case of the sieves also incorporated into an inorganic matrix, and gas-phase, aromatic primary amine mono N-alkylation processes using such catalyst compositions comprising contacting an aromatic primary amine with an alcohol or ether under N-alkylation conditions with such catalyst compositions to form a product containing substantially an N-alkyl monosubstituted aromatic amine.

N-alkylamines, particularly N-methyl and N-ethyl anilines, and their N,N'-dialkyl analogues can be useful in small amounts as additives to gasoline in that they substantially improve the octane rating of gasoline. The small amount required to be added to gasoline for the considerable octane boost obtained is generally not enough to increase materially the NOX emission and hence interest has been shown in their use in octane enhancement of liquid transportation fuels.

N-alkylated amines have been made by a number of Japanese workers by both liquid- and gas-phase processes; for example, N-N'-dimethylamines in yields up to 98% have been made by the liquid-phase reaction of aromatic amines with methanol in the presence of a water-insoluble, silica-alumina catalyst. See Japanese Patent 49081331. A series of N-alkylanilines has been produced by reaction of aniline with an alcohol in the gas phase with either a boron-aluminum or iron phosphate catalyst. See Japanese Patent 54081228. Shell in U.S. Pat. No. 2,580,284 teaches the use of Cu/Zn oxides to alkylate aniline to N-methylaniline in the presence of hydrogen. In addition N-alkyl amines have been made by reacting an aromatic primary amine with an alcohol or ether in the gas phase with silica-alumina catalysts in which the silica content is controlled to between 1-10 weight percent. This reference, Japanese Patent 53090227, teaches the use of aromatic amines such as toluidine, aniline, ethyl aniline, xylidine, pseudocumene, etc., as well as such alcohols as ethyl, n-propyl, butyl, amyl and hexyl alcohols and their corresponding ethers.

A number of recent patents have claimed the formation of gallosilicate-type molecular sieves or gallium compound impregnated/exchanged sieves of various structures which are said to be useful for a variety of catalytic purposes. For example, U.S. Pat. Nos. 4,372,930 and 4,450,312 teach gallosilicate molecular sieves of Structure Types Nu-3 and Nu-5 which are claimed to be useful for the selective alkylation of alkanes and the isomerization of xylenes, respectively. U.S. Pat. No. 4,444,652 teaches the formation of gallium compound impregnated/exchanged sieves for upgrading low grade gasolines. In U.S. Pat. No. 4,377,502, the alkylation of toluene using a variety of crystalline aluminosilicate sieves is set forth. The patent teaches that the aluminum may be substituted by gallium. And in U.S. Pat. No. 4,276,437, ZSM-5 molecular sieve catalyst compositions impregnated with gallium and phosphorus compounds are taught for the selective paraethylation of toluene.

Both monosubstituted and disubstituted N-alkyl aromatic amines have various uses but the disubstituted variation, which is the easiest to make pure, claims most of the uses. Monosubstituted N-alkylamines are however of interest as are improved methods of making them. Now a catalysed gas-phase method has been found which, using the proper catalyst, and under proper temperature and molar ratio of reactant conditions is able to make substantial quantities of the monosubstituted compound at reasonable conversions.

SUMMARY OF THE INVENTION

Described herein are processes comprising contacting an aromatic primary amine selected from the group consisting of aniline, ring-substituted anilines, aminonaphthalene and ring-substituted aminonaphthalenes with a $C_1$ to $C_5$ alcohol or ether under N-alkylation conditions with a catalyst composition comprising a supported or unsupported crystalline, molecular sieve or an unsupported amorphous silica-alumina containing at least about forty (40) weight percent $SiO_2$ to form a product which is substantially a mono N-alkylated aromatic amine. Also, described herein are the use of unsupported, crystalline Y-type sieves, supported and unsupported crystalline AMS-1B borosilicates, zeolites, gallosilicates, zincosilicates and unsupported amorphous silica-aluminas as catalyst compositions for the inventive process.

DETAILED DESCRIPTION OF THE INVENTION

In carrying out the process of the instant invention, one reactant is an aromatic primary amine such as aniline, a ring-substituted aniline, aminonaphthalene or ring substituted aminonaphthalene. Lower alkyl ($C_1$ to $C_5$) alkoxy, hydroxy, nitro and the like groups may be substituted on the ring. In general, if substituted, the ring is only monosubstituted. In the naphthalenes, the amino group can be either in the alpha or the beta position. Aniline and alpha- or beta-aminonaphthalene are preferred reactants.

The other reactant is a $C_1$ to $C_5$ lower alcohol or ether containing $C_1$ to $C_5$ alkyl groups. Such alcohols as methanol, ethanol, propanol, isopropanol, 1-butanol, 2-butanol, t-butyl alcohol, 1-pentanol, 2-pentanol and the like are useful. Methanol is preferred. Ethers such as dimethyl ether, methyl ethyl ether, methyl pentyl ether, and dipentyl ether are also useful. Preferred among the ethers is dimethyl ether.

The gallosilicate crystalline molecular sieves used in this invention are characterized by the representative X-ray pattern listed in Table A below and by the composition formula:

$$0.9 \pm 0.2 \, M_{2/n}O : Ga_2O_3 : ySiO_2 : zH_2O$$

wherein M is at least one cation, n is the valence of the cation, y is between 4 and about 600, and z is between 0 and about 160. It is believed that the small gallium content of the sieves is at least in part incorporated in the crystalline lattice. Various attempts to remove the gallium from the gallosilicate sieves by exhaustive exchange with sodium, ammonium, and hydrogen ions were unsuccessful and therefore, the gallium content is considered nonexchangeable in the instant sieves.

TABLE A

| d-Spacing Å (1) | Assigned Strength (2) | d-Spacing Å (1) | Assigned Strength (2) |
|---|---|---|---|
| 11.10 ± 0.20 | VS | 3.84 ± 0.10 | MS |
| 9.96 ± 0.20 | MS | 3.71 ± 0.10 | M |
| 6.34 ± 0.20 | W | 3.64 ± 0.10 | W |
| 5.97 ± 0.20 | W | 2.98 ± 0.10 | VW |
| 5.55 ± 0.20 | W | | |
| 4.25 ± 0.10 | VW | | |

(1) Copper K alpha radiation
(2) VW = very weak; W = weak; M = medium; MS = medium strong; VS = very strong The gallosilicate molecular sieve useful in this invention can be prepared by crystallizing an aqueous mixture, at a controlled pH, of a base, a gallium ionaffording material, an oxide of silicon, and an organic template compound, and, optionally, a gallium mineralizing agent such as 2,4-pentanedione.

Typically, the mol ratios of the various reactants can be varied to produce the crystalline gallosilicates of this invention. Specifically, the mol ratios of the initial reactant concentrations are indicated below:

| | Broad | Preferred | Most Preferred |
|---|---|---|---|
| $SiO_2/Ga_2O_3$ | 4-200 | 10-150 | 20-100 |
| Base/$SiO_2$ | 0.5-5 | 0.05-1 | 0.1-0.5 |
| $H_2O/SiO_2$ | 5-80 | 10-50 | 20-40 |
| Template/$SiO_2$ | 0-1 | 0.01-0.2 | 0.02-0.1 |
| Mineralizer/$Ga_2O_3$ | 5-100 | 10-30 | 20-60 |

By regulation of the quantity of gallium (represented as $Ga_2O_3$) in the reaction mixture, it is possible to vary the $SiO_2/Ga_2O_3$ molar ratio in the final product. In general, it is desirable to have content of the gallo-silicate sieve of this invention between about 0.1 and about 8 percent by weight of gallium. More preferably, the amount of gallium should be between about 0.2 and about 6 weight percent gallium and, most preferably, between about 0.3 and about 4 weight percent of gallium. Too much gallium in the reaction mixture appears to reduce the sieve crystallinity which reduces the catalytic usefulness of the sieve.

More specifically, the material useful in the present invention is prepared by mixing a base, a gallium ion-affording substance, optionally a gallium mineralizing agent, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing, the final pH is reached by addition of the base, and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.5 and 11.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water insoluble gallium compounds such as the oxide can be used as well. Gallium nitrate is the preferred source of gallium.

Gallium mineralizing agents which are used optionally include ketones, alcohols or organic esters, such as ethanol, butanol, ethylene glycol, methyl ethyl ketone, or 2,4-pentanedione. The latter compound is preferred.

Cations useful in formation of the gallosilicate sieves include the sodium ion and the ammonium ion. The sieves also can be prepared directly in the hydrogen form with an organic base such as ethylenediamine.

The acidity of the gallosilicate sieves of this invention is high as measured by the Hammett $H_o$ function which lies in the neighborhood of about $-3$ to about $-6$.

Organic templates useful in preparing the crystalline gallosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline gallosilicate molecular sieve can be prepared by crystallizing a mixture of sources for an oxide of silicon, an oxide of gallium, optionally a mineralizing agent such as 2,4-pentanedione, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. If used, the molar ratio of 2,4-pentanedione to gallium should be above about 2.5 and below about 50. More preferably, the molar ratio lies between about 5 and about 40 and, most preferably about 10 and about 30. The molar ratio of base to silicon oxide should be about above about 0.5, typically below about 5, preferably between about 0.05 and about 1.0 and most preferably between about 0.1 and about 0.5. The molar ratio of alkylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 25 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 150° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° C. to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C for about 16 hours and is then calcined in air in a manner such that the temperature rise does not exceed 125° C. per hour until a temperature of about 540° C. is reached. Calcination at this temperature usually is continued for about 4 hours. The gallosilicate sieves thus made generally have a surface area greater than about 300 sq. meters per gram as measured by the BET procedure.

The gallosilicate sieve useful in this invention is admixed with or incorporated within various binders or matrix materials depending upon the intended process use. The crystalline gallosilicates are combined with active or inactive materials, synthetic or naturally occurring zeolites, as well as inorganic or organic materials which would be useful for binding the gallosilicate. Well-known materials include silica, silica-alumina, alumina, magnesia, titania, zirconia, alumina sols, hydrated aluminas, clays such as bentonite or kaolin, or other binders wellknown in the art. Typically, the gallosilicate is incorporated within a matrix material by blending with a sol of the matrix material and gelling the resulting mixture or slurrying the sieve with the matrix material and drying. Also, solid particles of the gallosilicate and matrix material can be physically admixed. Typically, such gallosilicate compositions can be pelletized or extruded into useful shapes. The crystalline gallosilicate content can vary anywhere from a few up to 100 weight percent of the total composition. Catalytic compositions can contain about 0.1 weight percent to about 100 weight percent crystalline gallosilicate material and preferably contain about 10 weight percent to about 95 weight percent of such material and most preferably contain about 20 weight percent to about 80 weight percent of such material.

Silica-supported gallosilicate catalyst compositions which are preferred can be made by dry mixing the gallo-silicate sieve with a silica source such as Cab-O-Sil, adding water and stirring. The resulting solid is then dried below about 200° C. and finally calcined between about 350° C. and 700° C.

Some of the catalyst compositions used in this invention are based on the AMS-1B crystalline borosilicate molecular sieve, which is described in U.S. Pat. Nos. 4,268,420, 4,269,813 and 4,285,919 and Published European Patent Application 68,796, all incorporated herein by reference. Other catalyst compositions used in this invention are described in U.S.S.N. 814,646, filed Dec. 30, 1985 (zincosilicates), also incorporated herein by reference.

Amorphous silica-aluminas are well-known in the art and require no further descriptions here. In general, those silica-aluminas containing more than about forty (40) weight percent $SiO_2$ by weight are preferred, and those containing more than about sixty (60) weight percent are more preferred. Most preferred are silica-aluminas containing more than about seventy-five (75) weight percent.

N-alkylation of aromatic primary amines in the presence of the above-described catalyst compositions is effected by contact of the aromatic amine with an alcohol or its corresponding ether in the gas phase, at a temperature between about 200° C. and about 500° C. and preferably between about 300° C. and about 400° C.

The reaction generally takes place at atmospheric pressure, but the pressure may be within the approximate range of about 1 atmosphere to about 1000 psig, more preferably between about 50 psig and about 500 psig.

The molar ratio of aromatic primary amine to alcohol or ether employed is within the approximate range of about 0.1 to about 10, more preferably about 0.2 to about 2 and most preferably about 0.5 to about 1.5. Reaction is suitably accomplished utilizing a weight hourly space velocity of between about 0.1 and about 100 and preferably between about 0.5 and about 50.

The product of the N-alkylation reaction of the instant invention substantially contains the mono-alkylated product. By substantial is meant more than about forty (40) percent by weight mono-alkylated amine, more preferably more than about sixty (60) percent by weight mono-alkylated amine and most preferably, more than about seventy (70) weight percent mono-alkylated amine.

The reaction product, consisting of the N-alkylated amine with comparatively smaller amounts of the corresponding N,N'-dialkyl aromatic amine, generally need not be separated for use as an octane enhancer for gasoline. Separation of the monoalkylated compound, if desired, can be accomplished by an efficient fractionation tower as some reactants and products tend to be close together in boiling point.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

The N-alkylation reactions of Example 5 below were carried out in a glass reactor of plug-flow design. Reactants in various mol ratios, aniline to methanol, were mixed, fed into a preheater, and swept with a stream of nitrogen into a ½inch O.D. ± 5-inch reactor tube filled with a 2-5 g catalyst composition charge. The entire reactor was heated in a Lindberg furnace maintained at reaction temperature. Product was collected in a cooled vessel as it dripped from the reactor and was analyzed by gas chromatography on a 6 ft. glass column packed with Apiezon-L.

In addition to N-methylaniline each product produced in Example 6 below was also found to contain various amounts of unreacted aniline and N,N-dimethylaniline.

EXAMPLE 1

A 33.54 g portion of gallium nitrate was dissolved in water and to the solution was added 53.66 g of 2,4-pentanedione (AA) and 49.40 g of tetrapropylammonium bromide (TPA Br). After the AA and TPA Br had dissolved, a 352.03 g portion of Ludox AS-40 and a 37.35 g portion of sodium hydroxide were added. The resulting mixture which had a pH of 10.95 was transferred to a stainless steel autoclave and digested at 152° C. After 7 days digestion, the autoclave contents were filtered, and the solid material washed with water and dried at 165° C. for about 6 hours. The dried solid was calcined at 538° C. for 12 hours. The calcined solid was exchanged twice with a concentrated ammonium acetate solution and dried at 165° C. The sieve was analyzed and contained 3.94 weight percent gallium and 42.5 weight percent of silicon. It had a BET surface area of 345 sq m/g and a micropore volume of 0.126 cc/g. A list of d-spacings and relative intensities from XRD for this sieve having an MFI-type structure follows below in Table B.

TABLE B

| d-Spacing Å (1) | Assigned Strength | d-Spacing Å (1) | Assigned Strength |
|---|---|---|---|
| 11.0728 | VS | 2.6022 | VW |
| 3.8353 | MS | 1.6668 | VW |
| 9.9597 | M | 1.8685 | VW |
| 3.7055 | M | 5.3352 | VW |
| 3.6352 | W | 2.3925 | VW |
| 5.9620 | W | 3.3749 | VW |
| 6.3266 | W | 1.9486 | VW |
| 5.5470 | W | 1.6598 | VW |
| 2.9755 | VW | 1.4606 | VW |
| 4.2428 | VW | 2.4105 | VW |
| 3.2986 | VW | 2.7267 | VW |
| 4.3415 | VW | 2.5053 | VW |
| 3.0431 | VW | 3.9942 | VW |
| 5.6738 | VW | 5.1100 | VW |
| 6.6657 | VW | 1.3922 | VW |
| 2.0057 | VW | 2.5856 | VW |
| 3.4297 | VW | 7.3990 | VW |
| 1.9911 | VW | 1.9164 | VW |
| 3.3380 | VW | 1.4520 | VW |
| 4.9631 | VW | | |
| 3.3192 | VW | | |
| 2.9343 | VW | | |
| 4.5904 | VW | | |
| 10.5679 | VW | | |
| 3.4662 | VW | | |
| 2.4841 | VW | | |
| 2.3859 | VW | | |

(1) Copper K alpha radiation

EXAMPLE 2

A 11.6 g portion of gallium nitrate slurried in water was added to 41.52 g of 2,4-pentanedione (AA) and 38.33 g of 1,9-diaminononane (DAN). After the AA and DAN had dissolved, a 222.70 g portion of Ludox AS-40 and a 17.0 g portion of sodium hydroxide were added. The resulting mixture which had a pH of 10.5 was transferred to a stainless steel autoclave and digested at 177° C. After 18 days digestion, the autoclave content was filtered, and the solid material washed with water and dried at 165° C. for about 6 hours. The dried solid was calcined at 538° C. for 12 hours. The calcined solid was exchanged twice with a concentrated ammonium acetate solution, dried at 165° C., and calcined again at 538° C. for 4 hours. The sieve was analyzed and found to contain 1.96 weight percent gallium and 41.76 weight percent silicon. It had a BET surface area of 130 sq m/g and a micropore volume of 0.031 cc/g. Using XRD the sieve was indexed to a TON-type structure.

EXAMPLE 3

A 1.59 g portion of gallium oxide slurried in water was added to 37.30 g of 2,4-pentanedione (AA) and 35.78 g of tetrapropylammonium bromide (TPA Br). After the AA and TPA Br had dissolved, a 252.30 g portion of Ludox AS-40 and a 15.2 g portion of sodium hydroxide were added. The resulting mixture which had a pH of 10.35 was transferred to a stainless steel autoclave and digested at 151° C. After 21 days digestion, the autoclave content was filtered, and the solid material washed with water and dried at 151° C. for about 6 hours. The dried solid was calcined at 538° C. for 12 hours. The calcined solid was exchanged twice with a concentrated ammonium acetate solution and dried at 165° C. The sieve was analyzed and found to contain 0.85 weight percent gallium and 43.08 weight percent silicon. It had a BET surface area of 337 sq m/g and a micropore volume of 0.0173 cc/g. Its XRD pattern was indexed to an MFI-type structure.

EXAMPLE 4

A 10 g portion of the sieve of Example 1 and 15.0 g Cab-O-Sil silica were dry mixed and transferred to a crystallizing dish with sufficient water to form a slurry. The mixture was heated at 150° C. until it gelled. The gel was dried at 130° C. for 16 hours and calcined at 600° C. On cooling, the catalyst composition was ground to 18/40 mesh. This catalyst composition was 40% by weight gallo-silicate sieve and 60% by weight γ-alumina.

EXAMPLE 5

A 44.55 g portion of the sieve of Example 3 was ground to a fine powder and dry mixed with 66.44 g of Cab0-Sil silica. Distilled water was added to part of this solid until a solids to water ratio of 1 was reached. Additional solid was added until the mixture was thixotropic. Further solids were added until large particles formed. These particles were dried at 165° C. for 4 hours and then calcined at 482° C. for 4 hours. The resulting solid was then ground to an 18/40-mesh powder. This catalyst composition was 40% by weight gallosilicate sieve and 60% by weight γ-alumina.

EXAMPLE 6

The data in Table C. below was collected using the procedure under General above.

TABLE C

| Aniline Alkylation to N-methylaniline with Methanol | | | | |
|---|---|---|---|---|
| Catalyst Type | Temp °C. | Mols Aniline/ Mol Methanol | Conversion % | Selectivity % |
| [1]LZ-Y82 | 300 | 1/0.5 | 75 | 74 |
| | | 1/0.75 | 59 | 83 |
| | | 1/2 | 82 | 38 |
| | | 1/4 | 87 | 38 |
| [1]LZ-Y72 | 300 | 1/0.5 | 45 | 38 |
| | | 1/0.75 | 59 | 63 |
| | | 1/2 | 86 | 43 |
| [1]LZ-Y62 | 300 | 1/0.5 | 65 | 62 |
| | | 1/0.75 | 60 | 70 |

TABLE C-continued

Aniline Alkylation to N-methylaniline with Methanol

| Catalyst Type | Temp °C. | Mols Aniline/ Mol Methanol | Conversion % | Selectivity % |
|---|---|---|---|---|
| | | 1/2 | 89 | 40 |
| | | 1/4 | 90 | 42 |
| [3]HAMS-1B on $\gamma$-Al$_2$O$_3$ | 300 | 1/0.75 | 65 | 64 |
| Example 4 | 400 | 1/0.5 | 40 | 81 |
| | | 1/0.75 | 56 | 90 |
| | | 1/2 | 51 | 89 |
| | | 1/4 | 50 | 93 |
| [4]Example 2 | 400 | 1/0.75 | 44 | 77 |
| | | 1/2 | 43 | 79 |
| Example 5 | 400 | 1/0.75 | 32 | 84 |
| [2]Amorphous Silica-Alumina | 300 | 1/0.75 | 79 | 66 |

[1]Y-type sieves product of Union Carbide Corporation LZ-Y82, LZ-Y72 and LZ-Y62 are 72.2%, 72.7%, and 64.9% by weight SiO$_2$, respectively.
[2]Product of Stream Chemical, Inc. (87% SiO$_2$ and 12% Al$_2$O$_3$)
[3]40% by weight sieve and 60% by weight $\gamma$-alumina
[4]Unsupported gallosilicate sieve

EXAMPLE 7

Various samples of product from Example 6 were used without separation of the major component, mono N-alkylated aniline, to enhance the octane of commercial gasoline. Based upon tests with unleaded regular and unleaded premium, the (R+M)/2 octane gains for 0.25 volume percent addition were respectively 0.3 and 0.6. Further tests showed that the alkylated aniline product addition had little effect on existent gum and oxidation stability.

What is claimed is:

1. A gas-phase process comprising contacting an aromatic primary amine selected from aniline and ring-substituted aniliens with a $C_1$ to $C_5$ alcohol or ether under N-alkylation conditions with a gallosilicate molecular sieve to form a product which is substantially a mono N-alkylated aromatic amine.

2. The process of claim 1 wherein said sieve is composited in an alumina matrix.

3. The process of claim 1 wherein said aromatic primary amine is aniline.

4. The process of claim 3 wherein said $C_1$ to $C_5$ alcohol or ether is methanol.

5. The process of claim 4 wherein said sieve provides an X-ray pattern comprising the following X-ray diffraction lines and assigned strengths.

| Interplanar Spacing d, Å | Assigned Strength | Interplanar Spacing d, Å | Assigned Strength |
|---|---|---|---|
| 11.10 0.20 | VS | 4.25 0.10 | VS |
| 9.96 0.20 | MS | 3.84 0.10 | MS |
| 6.34 0.20 | W | 3.71 0.10 | M |
| 5.97 0.20 | W | 3.64 0.10 | W |
| 5.55 0.20 | W | 2.98 0.10 | VW |

* * * * *

UNITED STATES PATENT AND TRADEMARK OFFICE
CERTIFICATE OF CORRECTION

PATENT NO. : 5,159,115
DATED : Oct. 27, 1992
INVENTOR(S) : Peter G. Pappas, et al It is certified that error appears in the above-indentified patent and that said Letters Patent is hereby corrected as shown below:

| Col. | Line | |
|------|------|---|
|      |      | On the title page "[21] Appl. No.: 397,379" should read --[21] Appl. No.: 396,379-- |
| 5    | 43   | "wellknown in the art." should read --well-known in the art--. |
| 7    | 60   | "38.33g of" should read --48.33g of--. |
| 8    | 44   | "CabO-Sil silica" should read --Cab-O-Sil silica--. |
| 10   | 6    | "substituted aniliens" should read --substituted anilines--. |

Signed and Sealed this

Sixteenth Day of August, 1994

Attest:

BRUCE LEHMAN

Attesting Officer

Commissioner of Patents and Trademarks